(12) United States Patent
Frey et al.

(10) Patent No.: US 8,398,612 B2
(45) Date of Patent: Mar. 19, 2013

(54) CATHETER FOR VASCULAR ACCESS AND METHOD FOR MANUFACTURING THE SAME

(75) Inventors: Helmut Frey, Williamsburg, VA (US); Ingolf Dieringer, Hechingen-Stetten (DE); Uwe Ruhl, Hechingen-Boll (DE)

(73) Assignee: Gambro Lundia AB, Lund (SE)

( * ) Notice: Subject to any disclaimer, the term of this patent is extended or adjusted under 35 U.S.C. 154(b) by 887 days.

(21) Appl. No.: 11/718,459

(22) PCT Filed: Nov. 5, 2004

(86) PCT No.: PCT/IB2004/003626
§ 371 (c)(1), (2), (4) Date: Mar. 14, 2008

(87) PCT Pub. No.: WO2006/048700
PCT Pub. Date: May 11, 2006

(65) Prior Publication Data
US 2009/0069792 A1    Mar. 12, 2009

(51) Int. Cl.
*A61M 25/16* (2006.01)
*A61M 39/00* (2006.01)
(52) U.S. Cl. .......................... 604/533; 604/535
(58) Field of Classification Search ................. 604/535, 604/533, 103, 236, 247
See application file for complete search history.

(56) References Cited

U.S. PATENT DOCUMENTS

| | | |
|---|---|---|
| 4,670,009 A | 6/1987 | Bullock |
| 4,875,481 A | 10/1989 | Higgins |
| 4,925,450 A | 5/1990 | Imonti et al. |
| 4,969,875 A | 11/1990 | Ichikawa |
| 5,041,083 A | 8/1991 | Tsuchida et al. |
| 5,041,097 A | 8/1991 | Johnson |
| 5,066,285 A | 11/1991 | Hillstead |
| 5,135,502 A | 8/1992 | Koenig, Jr. et al. |
| 5,143,409 A | 9/1992 | Lalikos |
| 5,156,594 A | 10/1992 | Keith |
| 5,167,647 A | 12/1992 | Wijkamp et al. |
| 5,178,803 A | 1/1993 | Tsuchida et al. |
| 5,380,301 A | 1/1995 | Prichard et al. |
| 5,395,316 A | 3/1995 | Martin |
| 5,403,284 A | 4/1995 | Gross |

(Continued)

FOREIGN PATENT DOCUMENTS

| | | |
|---|---|---|
| EP | 0 366 794 A1 | 5/1990 |
| EP | 0 937 480 A1 | 8/1999 |

(Continued)

*Primary Examiner* — Kevin C Sirmons
*Assistant Examiner* — Imani Hayman
(74) *Attorney, Agent, or Firm* — Pearne & Gordon LLP (57) ABSTRACT

Catheter (1) for vascular access comprising a cannula (2) having at least one first lumen (21), at least one first connection tube (3), and a connection molded simultaneously on an end of the cannula (2) and on at least one part of the first connection tube (3) and manufacturing process comprising the following stages: taking a cannula (2) having at least one first lumen (21), taking one first connection tube (3), placing in a mould one end of the cannula (2) and one end of the first connection tube (3), injecting into the mould a molding material to obtain the connection (4) between the end of the first connection tube (3) and the end of the cannula placing the first lumen (21) and at least the first tube (3) in fluid communication and device for implementing the manufacturing process.

12 Claims, 8 Drawing Sheets

U.S. PATENT DOCUMENTS

| | | |
|---|---|---|
| 5,466,230 A | 11/1995 | Davila |
| 5,480,380 A | 1/1996 | Martin |
| 5,718,678 A | 2/1998 | Fleming, III |
| 5,800,410 A | 9/1998 | Gawreluk |
| 5,830,401 A | 11/1998 | Prichard et al. |
| 5,906,598 A | 5/1999 | Giesler et al. |
| 5,961,485 A | 10/1999 | Martin |
| 6,022,339 A | 2/2000 | Fowles et al. |
| 6,174,300 B1 | 1/2001 | Kriesel et al. |
| 6,290,265 B1 | 9/2001 | Warburton-Pitt et al. |
| 6,325,775 B1 | 12/2001 | Thom et al. |
| 6,481,980 B1 | 11/2002 | Vandlik et al. |
| 6,511,472 B1 | 1/2003 | Hayman et al. |
| 6,551,273 B1 | 4/2003 | Olson et al. |
| 6,575,959 B1 | 6/2003 | Sarge et al. |
| 7,261,708 B2 * | 8/2007 | Raulerson ............... 604/523 |
| 2001/0041881 A1 | 11/2001 | Sarge et al. |
| 2002/0050663 A1 | 5/2002 | Warburton-Pitt et al. |
| 2003/0088213 A1 | 5/2003 | Schweikert et al. |
| 2003/0088264 A1 | 5/2003 | Spohn et al. |
| 2003/0149395 A1 | 8/2003 | Zawacki |
| 2003/0220628 A1 | 11/2003 | Klisch et al. |
| 2004/0034324 A1 | 2/2004 | Seese et al. |
| 2004/0034333 A1 | 2/2004 | Seese et al. |
| 2004/0039409 A1 | 2/2004 | Coyle et al. |
| 2004/0054330 A1 | 3/2004 | Kurth et al. |
| 2004/0068239 A1 | 4/2004 | Utterberg et al. |
| 2004/0073171 A1 | 4/2004 | Rogers et al. |
| 2004/0164453 A1 | 8/2004 | Warburton-Pitt et al. |
| 2004/0164555 A1 | 8/2004 | Warburton-Pitt et al. |

FOREIGN PATENT DOCUMENTS

| | | |
|---|---|---|
| EP | 1 034 811 A1 | 9/2000 |
| WO | WO 03/033049 A2 | 4/2003 |
| WO | WO 2004/016301 A2 | 2/2004 |

* cited by examiner

CATHETER FOR VASCULAR ACCESS AND METHOD FOR MANUFACTURING THE SAME

BACKGROUND OF THE INVENTION

The present invention relates to a catheter for vascular access and to a method for manufacturing the same.

STATE OF THE PRIOR ART

Using catheters for intravascular access has become more and more spread when there is the need of withdrawing and/or injecting blood for treating different types of illnesses. One known application of vascular access catheters is in extracorporeal blood treatment such as particularly hemodialysis, hemofiltration, hemodiafiltration, ultrafiltration treatments where blood is taken from the patient, and extracorporeally treated before being reinjected into the patient during the same session.

In general, a catheter to inject or remove fluids can be located at different access points in the patient. Such catheterization can be achieved by using a single catheter with multiple lumena. Catherization can also be achieved using separate single-lumen catheters inserted into two different incisions in the area to be catheterized.

The features of a catheter often vary according to the patient, the treatment and the medical application of the catheter. These features include particularly the material; the shape; the number of components used; the length, number, diameter, section and thickness of the lumena.

We are concerned here more particularly with catheters for extracorporeal blood treatment, which generally have the specific feature of being implanted in a venous access of the patient. Two types of catheter exist: temporary catheters that are implanted in the patient for less than 4 weeks and permanent catheters that can remain in the patient for months or years.

In extracorporeal blood treatment, there are principally three types of catheters depending on the location thereof in the patient: jugular catheters, femoral catheters and subclavian catheters. One example of a catheter with several lumena is a dual-lumen catheter, in which one lumen allows the fluid to be inserted into the patient and the other enables it to be extracted. Most of the time, in order to limit the number of accesses on the patient, a dual-lumen or triple-lumen catheter is implanted for hemodialysis: the first two lumena are used for the withdrawal of the blood leaving the patient to be treated by the dialysis machine, and for returning the treated blood to the patient. The third lumen often has a smaller section than the first two and enables injection of any specific liquid that the patient may need during treatment.

For sake of completeness it also to be noted that in the specific field of dialysis two different types of catheter exist: catheters for extracorporeal blood treatment dialysis and catheters for peritoneal dialysis.

It will be remembered that extracorporeal blood treatment dialysis is a treatment carried out by a machine and which requires the extraction and return of the patient's blood by a vascular access, for example via the jugular vein in the neck, when a catheter is used. On the other hand peritoneal dialysis is another method that is conducted inside the patient by injecting into the peritoneum a treatment liquid that acts inside the patient and then after a certain time by extracting this liquid from the peritoneum. This treatment implies implantation of a catheter in the abdomen.

In term of their manufacture, catheters for extracorporeal blood treatment dialysis are very often made of polyurethane or silicone; by contrast, the material used for peritoneal dialysis is silicone. For extracorporeal blood treatment dialysis, dual-lumen catheters are very often used, whereas for peritoneal dialysis catheters single lumen catheters are typically used.

In terms of length, the catheters for extracorporeal blood treatment dialysis are approximately 20 cm long (for adults) whereas peritoneal dialysis catheters are longer, being at least 22 cm in length. The diameter of the accesses of a catheter for extracorporeal blood treatment dialysis varies between 2 and 5 mm, whereas the access of a catheter for peritional dialysis is approximately 5 mm, Vascular access catheters present a generally straight cannula, while peritoneal catheter can have a pre-formed (curled, for example) end portion with specially shaped holes.

Several catheters embodiment are known in the art.

Patent application WO03033049 relates to a catheter for hemodialysis having a detachable hub. To connect and place in communication each lumen of the cannula with each connection tube, the invention disclosed in this document uses a hub made of two parts that are connected in a detachable manner to each other, particularly by means of a screw thread. This enables the connection tubes to be replaced without changing the cannula implanted in the patient.

Patent application WO2004016301 discloses a catheter for use in peritoneal dialysis that may have one or several lumena and a overmolded hub made for connecting an internal segment intended to be implanted in the patient and an external segment intended to be connected to the tubing set of a peritoneal dialysis system. This documents refers however to catheters having use and structure different from those object of the present invention.

Lastly, catheters for vascular access manufactured in polyurethane with a cannula comprising two D-shaped internal lumena are also known. The cannula is obtained by extrusion and an overmolded hub is connected to one end of this cannula. The overmolding onto the cannula requires positioning of a portion of the cannula in an injection mould and insertion into each lumen of a metal core so that two ports are formed in the mould, each port communicating with one respective lumen. Once the hub has been molded on the cannula it contains two outlet ports, each in fluid communication with the respective cannula lumen, provided for the insertion and attachment of two connection lines that are used for branching the catheter to the hemodialysis machine (for example). These two lines are connected to the molded hub by techniques as gluing or solvent bonding.

A first drawback of this manufacturing method consists in that during the production polyurethane additives (for example) are used to stabilize the raw material. These additives tend to release to the surface and create problems in term of strength of the connection obtained by cyclohexanone (for example) bonding of the two tubing lines to the hub.

Moreover, since the lines are produced from the same material (polyurethane, for example) as the body, these substances are present in the attaching areas where the cyclohexanone is used for the chemical bond. These substances leave a relatively remarkable residue that has to be removed with a specific cleaning solvent. This creates costs during production, may increase the percentage of rejected products and in any casde affects the quality of the finished product.

Thus on the one hand the connection between the hub and the connection components is not very strong mechanically and on the other hand an additional stage in the manufacturing process is required.

A second drawback inherent to this manufacturing method is that it is always necessary to pay particular attention to the external diameter of the two lines, which must remain within strict tolerances. A line with too large an external diameter creates insertion problems whereas too small an external diameter creates too much space between the port of the body and the line and may lead to an unsafe connection.

A third drawback that is inherent to this manufacturing method is that the size of connection tubes for insertion into the premolded hub will always be the same and cannot be 'customized' according to the section of the access tubes one may want to connect to the hub.

A fourth drawback that is inherent to this manufacturing method is that the release of gluing solvent cyclohexanone (for example) to the patient is undesired but unfortunately always present in case of solvent bonding techniques.

SUMMARY OF THE INVENTION

In order to simultaneously simplify the assembly process to reduce the percentage of rejects during manufacturing and to be able to produce catheters in several different sizes in a simple and inexpensive manner, the applicant proposes a catheter for vascular access that has a specific hub and a corresponding manufacturing process for catheters for corresponding vascular access.

In order to achieve these objects, according to the invention a catheter for vascular access is provided comprising a cannula having at least one first lumen, at least one first connection tube, connection means for placing at least the first lumen of the cannula in fluid communication with at least the first connection tube, the connection means being molded on one end of the cannula and on at least one part of the first connection tube.

The invention also relates to a manufacturing process for a catheter for vascular access comprising the following stages: taking a cannula having at least one first lumen, taking at least one first connection tube, placing in a mould at least one end of the cannula and at least one end of the first connection tube, injecting into the mould a molding material to obtain connection means between the end of the first connection tube and the end of the cannula placing in fluid communication the first lumen and at least the first tube.

Other advantages and features of the invention will become clear from reading the following disclosure.

SHORT DISCLOSURE OF THE DRAWINGS

Reference will be made to the attached drawings, wherein.

DETAILED DISCLOSURE OF EMBODIMENTS OF THE INVENTION

Catheter with Single-Lumen Cannula

Figure 1:
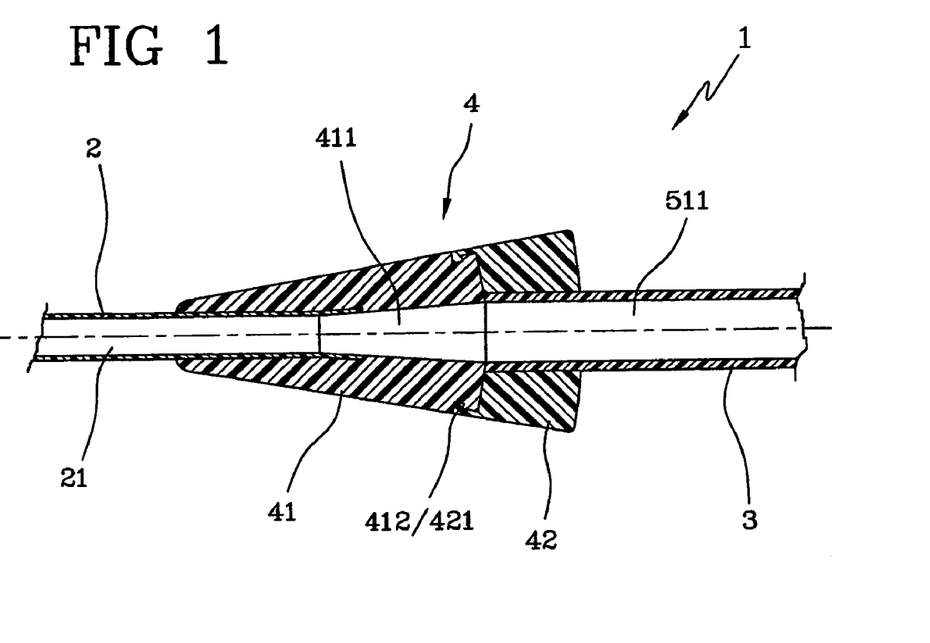
FIGS. 1, 2 and 3 show a longitudinal section view of three embodiments of a single-lumen catheter according to the present invention.
Figure 2:
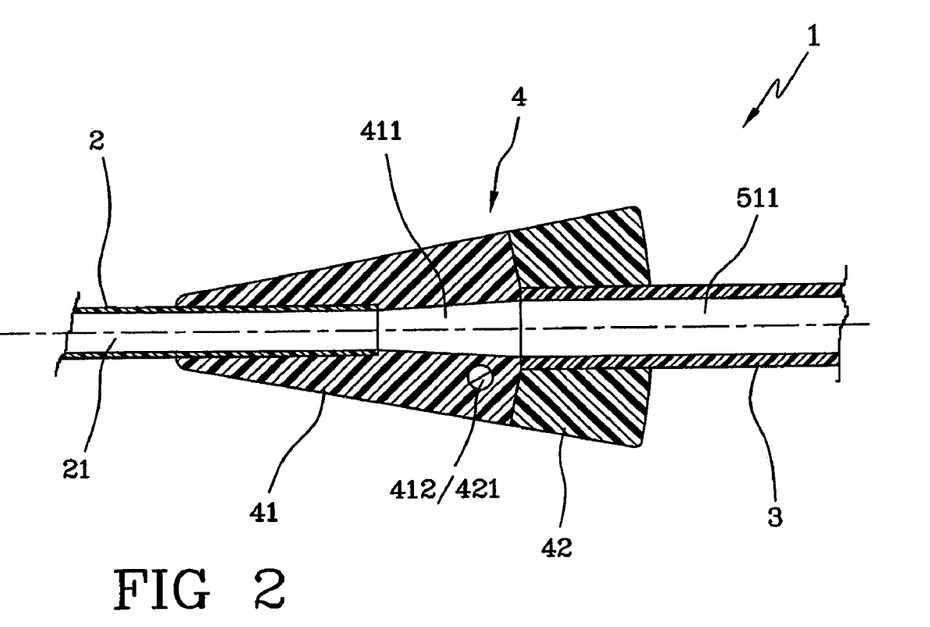
Figure 3:
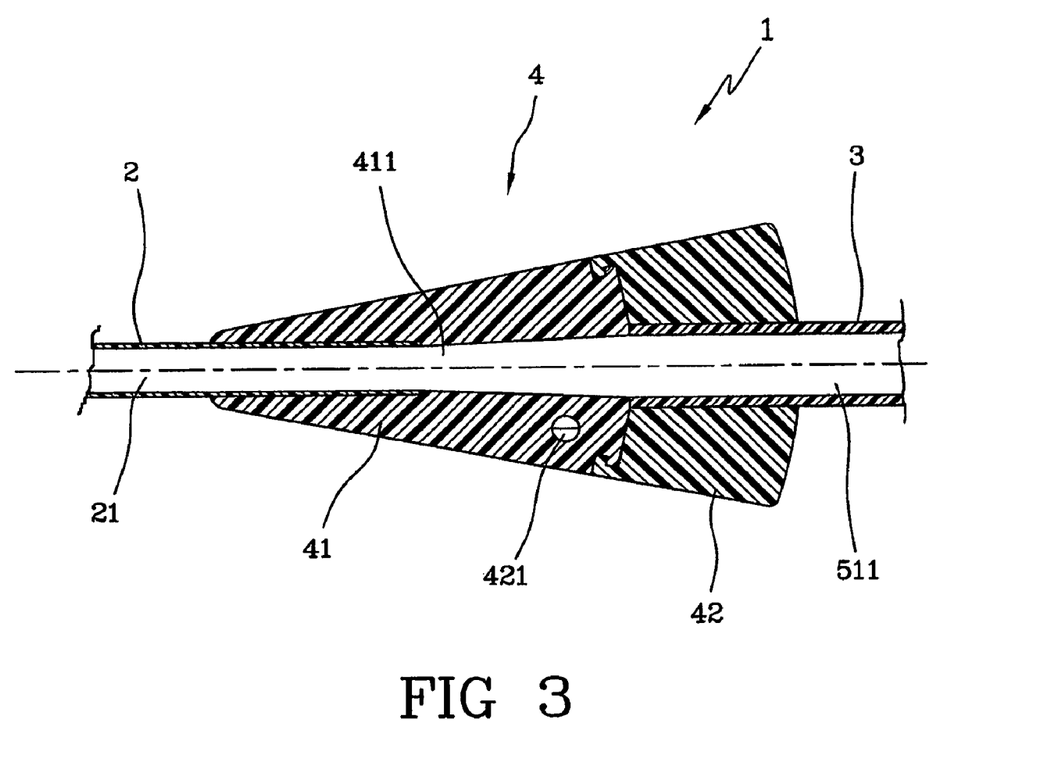
Figure 4:
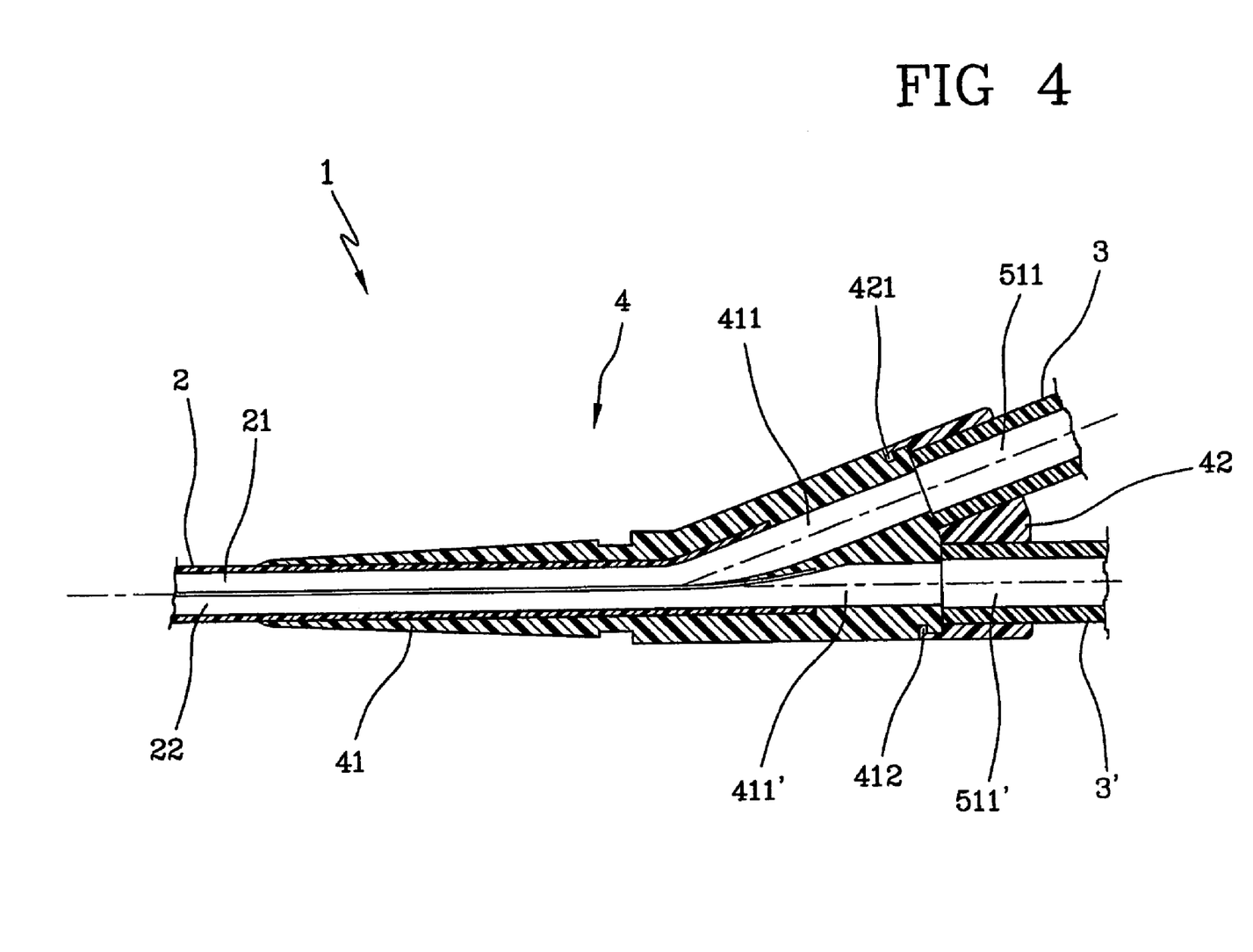
FIG. 4 is a section view of an embodiment of a dual lumen catheter according to the invention.

Reference will be made in this part to the different embodiments of a single-lumen catheter as shown in FIGS. 1 to 3.

FIG. 1 shows a catheter 1 for vascular access comprising a cannula 2 having at least one first lumen 21, at least one first connection tube 3, connection means 4 for placing at least the first lumen 21 of the cannula in fluid communication with at least the first connection tube 3; this connection means 4 is overmolded both on one end of the cannula 2 and on at least one part of the first connection tube 3. In this way, a single connection means simultaneously enables the cannula that will be implanted in the patient and the connection tubes that will be connected to the lines of the machine for extracorporeal blood treatment to be mechanically connected and placed in fluid communication.

The connection tubes may each comprise a clamp (not shown) and a luer-lock connector (not shown) that enable the tubes to be connected to the dialysis machine lines for all disclosed embodiments.

The product according to the invention is obtaining a hub on the cannula 2 and a connection to tube 3 by molding and no longer requires a further step of bonding of tube 3.

The connection means 4 comprises a first connection portion 41 molded on one end of the cannula 2. The first portion 41 defines the catheter hub and has at least one first passage 411 communicating with the first lumen 21 of the cannula and with tube end 511; the first passage 411 of hub 41 normally has a variable cross section, which in the present embodiment increases when approaching the tube 3 as this latter has a section grater then the cannula lumen.

A second connection portion 42 is overmolded on at least one part of the first connection portion 41 and on at least one part of the first connection tube 3 and insures the physical connection and necessary fluid seal between tube 3 and the hub 41. The second connection portion has a reduced axial extension and a tubular configuration; more in detail the axial extension of the second connection portion is much lower than the one of first connection portion or hub, and serves to obtain engagement of tube 3 to the same hub 41.

The second connection portion has an inner surface, which embraces an end of the tube 3, and has a frontal surface, which engages the hub 41. Notice the end of tube 3 presents a terminal face contacting an axially terminal face of hub 41 in correspondence of said passage 441.

In the embodiments shown, the second portion 41 just defines a collar of limited axial length extending exactly around end of tube 3.

The first and the second connection portions 41, 42 may comprise mechanical connection means cooperating together.

The mechanical connection means has at least one cavity 412, on the first connection portion 41, and at least one protuberance 421, on the second connection portion 42, the shape of which complements that of the cavity 412. These complementary shapes enable a very good mechanical connection.

The cavity 412 may take the form of an incision on at least one part surrounding the passage 411 of the first connection portion 41. The protuberance 421 will thus have the shape of a bead integral to the second connection portion 42 and inserted into the incision.

For example, the incision may extend on the first portion 41 all around passage 411: the mechanical connection is thus established all around each connection portion.

The incision may also take the shape of a groove in the first connection portion 41, i.e. a long and narrow incision. This incision may have a constant width and constitute a notch (more particularly a radial depression) in which the bead 421 will be overmolded during molding of the second connection portion. As shown in FIGS. 1 and 3, cavity 412 may comprise in longitudinal section a first part with a first depth and a second part with a different second depth. For example, in longitudinal section, the cavity could be L-shaped as in the mentioned drawings. Of course any other shape serving to guarantee good mechanical cooperation and to increase the cooperating surface between first and second connection portion would equivalently be suitable.

Alternatively, the cavity 412 may be a simple depression extending around the periphery of terminal face of hub 41 and be defined by a section reduction of hub 41.

Alternatively to or in combination with the incision-bead coupling, the connection means may have other mechanical attachments. The mechanical connection means may indeed comprise at least one cavity 413 on the first connection portion 41 defining a hole traversing at least partially the first connection portion 41 according to an axis transverse to the longitudinal axis of the first lumen 21 of the cannula, and at least one protuberance 422 on the second connection portion 42 the shape of which is complementary to that of the cavity 413 and which defines an arm traversing at least partially the hole of the first connection portion 41 and at least one of the ends of which is connected to the second portion 42. This possible mechanical connection is shown in FIGS. 2, 3, 7, 10 and 11. In the embodiment shown in exploded view of FIG. 10, cavity 413 is a through hole entirely transversely crossing the first connection portion. The arm shaped protuberance 422 entirely crosses the cavity as a sort of bar between the two connection portions 41 and 42.

These two connection methods herein referred to as 'incision-bead' and 'hole-arm' could be combined; in such a case the mechanical connection means would comprise: at least one cavity 413 on the first connection portion 41 defining a hole traversing at least partially the first connection portion 41 according to an axis transverse to the longitudinal axis of the first lumen of the cannula, at least one auxiliary cavity 412 on the first connection portion 41, at least one arm shaped protuberance 422 carried by the second connection portion 42, at least one auxiliary protuberance 421 carried by the second connection portion 42 the shape of which corresponds to that of the auxiliary cavity 412. FIG. 3 thus shows a single-lumen catheter with these two types of mechanical connection combined together.

If a catheter comprises the two above mechanical connection means combined together, any of the specific forms of the connection means disclosed above can be provided, namely: the auxiliary cavity 412 may have the shape of an incision on at least one part surrounding the first passage 411 of the first connection portion 41, and the auxiliary protuberance 421 may have the shape of a bead on at least one part of the second connection portion 42 surrounding at least the first connection tube 3. In the same way, the incision could entirely surround the first port and the bead surround the first connection tube 3. The incision may have the shape of a groove in the first connection portion 41. The auxiliary cavity 412 may extend exactly on the peripheral edge of the axially terminal face of the first portion 41.

More particularly, the auxiliary cavity 412 may comprise in longitudinal section a first part with a first depth and a second part with a different second depth or simply have a single constant depth.

Catheter with Dual-Lumen Cannula

Another group of embodiments will now be disclosed relating to catheters according to the invention comprising a dual-lumen cannula. These embodiments are shown in FIGS. 4 to 11. These dual-lumen catheters are proportionally much used for vascular access to the patient.

The catheter comprises at least one second lumen 22 in the cannula 2; at least one second connection tube 3', and the connection means places the second lumen of the cannula 22 in fluid communication with the second connection tube 3' and is molded on a part of the second connection tube 3'.

The connection means 4 comprises a first connection portion 41 molded on one end of the cannula 2. The first portion 41 defines the catheter hub and has at least one first passage 411, for communicating the first lumen 21 of the cannula with first tube 3, and a second passage 411', for communicating the second lumen 22 of the cannula 2 with tube end 511' of second connection tube 3'; normally the passages 411 and 411' have a variable cross section, which in the present embodiment increases when moving from the cannula to the tubes 3,3'. A second connection portion 42 is overmolded on at least one part of the first connection portion 41 and on at least one part of the first connection tubes 3 and 3' and insures the physical connection and necessary fluid seal between tubes 3, 3' and the hub 41. The second connection portion has a reduced axial extension; more in detail the axial extension of the second connection portion is much lower than the one of first connection portion or hub, and serves to obtain engagement of tube 3 to the same hub 41. The second connection portion has an inner surface, which embraces an end of the tube 3 and the end of tube 3', and has a frontal surface, which engages the hub 41. Notice the end of tube 3 as well the end of tube 3' present a terminal face contacting the hub 41 in correspondence of said second port. Practically the second portion 41 defines a two holes collar of limited axial length extending around the end of tubes 3, 3'.

Mechanical connection means are operating between the first and the second connection portions. In detail, with reference to the embodiment of FIG. 4 for instance, the mechanical connection means comprises a cavity 412 provided on first connection portion 41, which extends as a loop around the first passage 411 and the second passage 411'. A protuberance 421 carried by second connection portion 42, formed during overmolding of second portion onto the first portion, is counter-shaped to and perfectly engages into said cavity.

Figure 9:
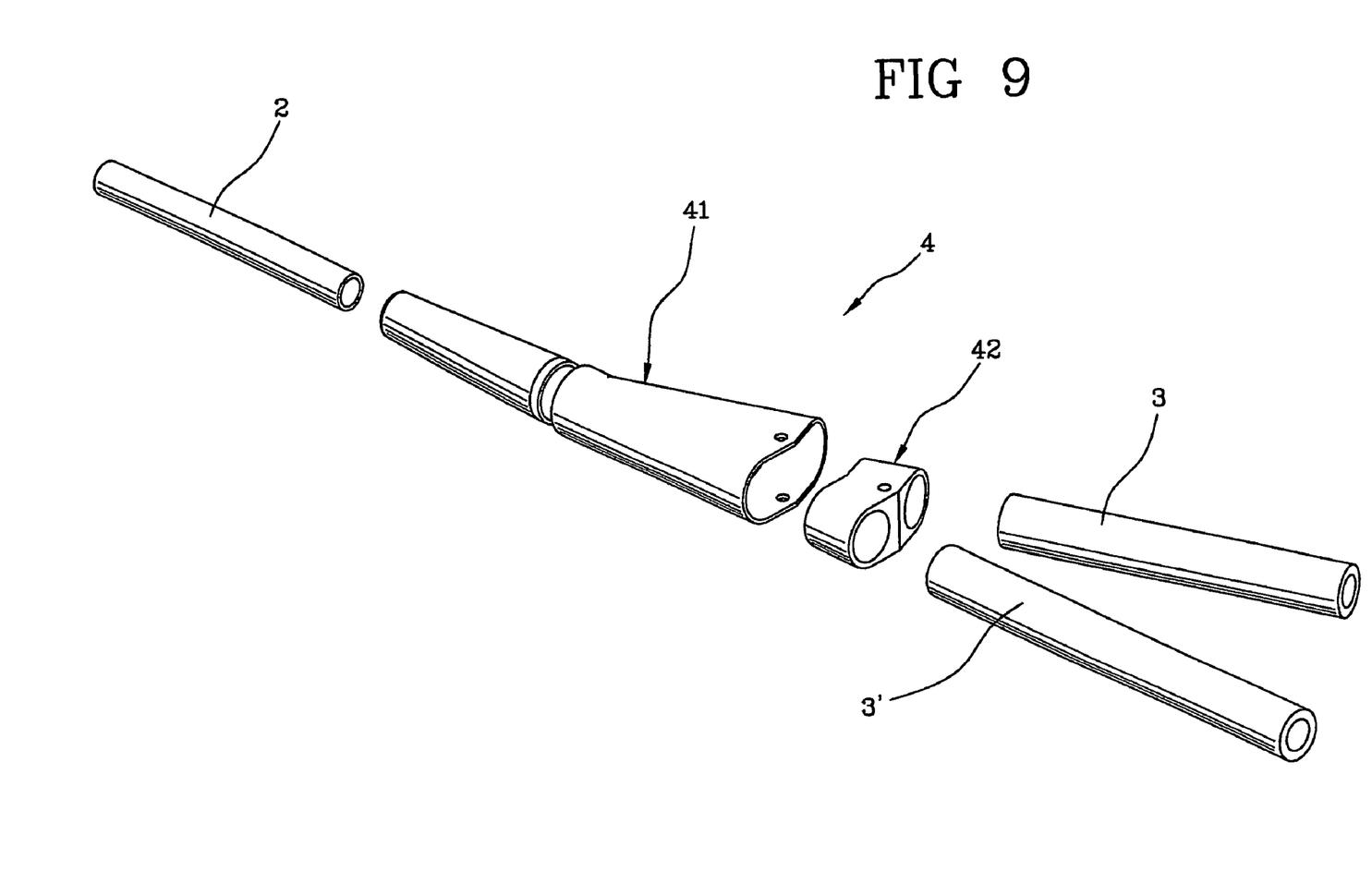
Figure 10:
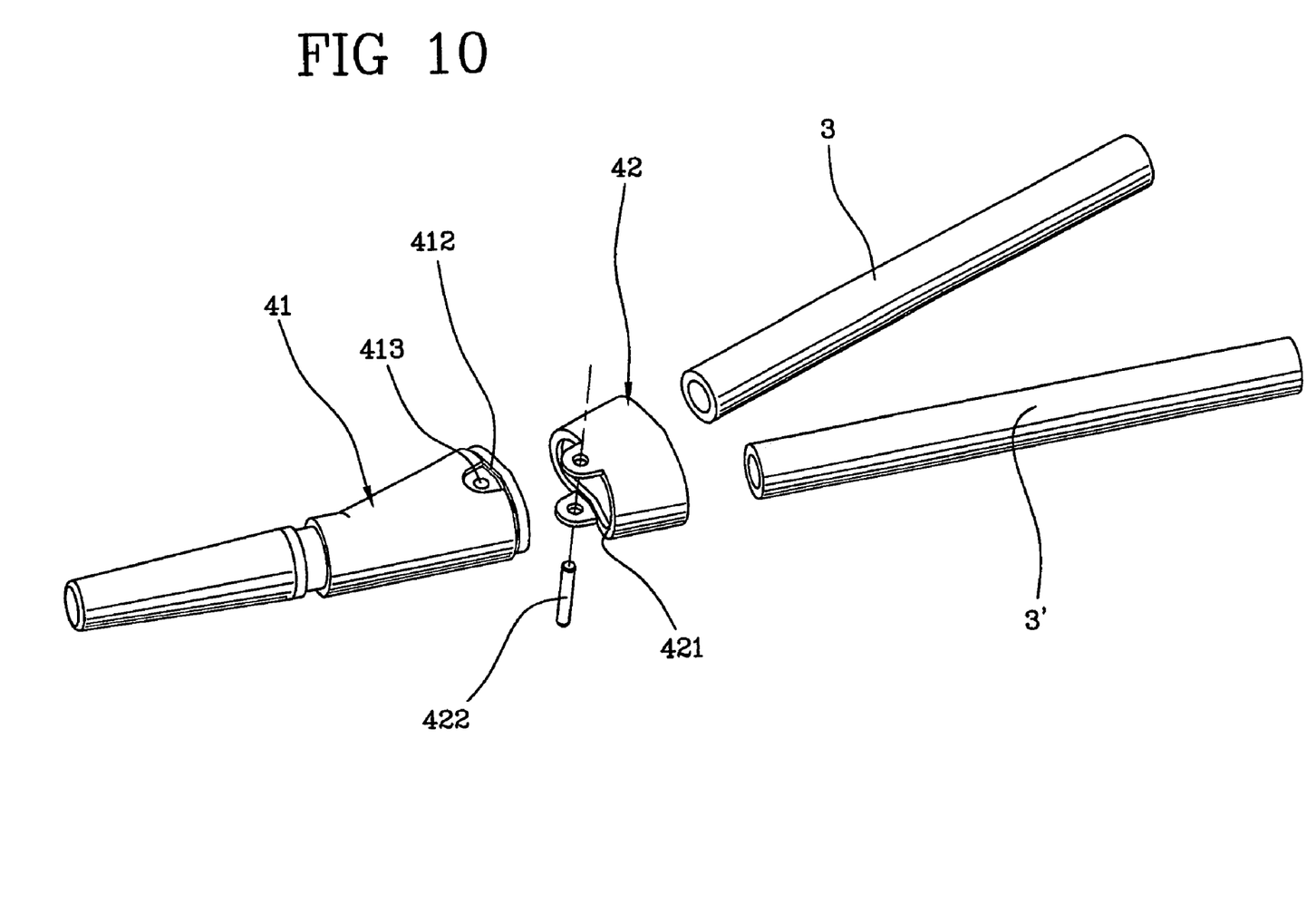
Figure 11:
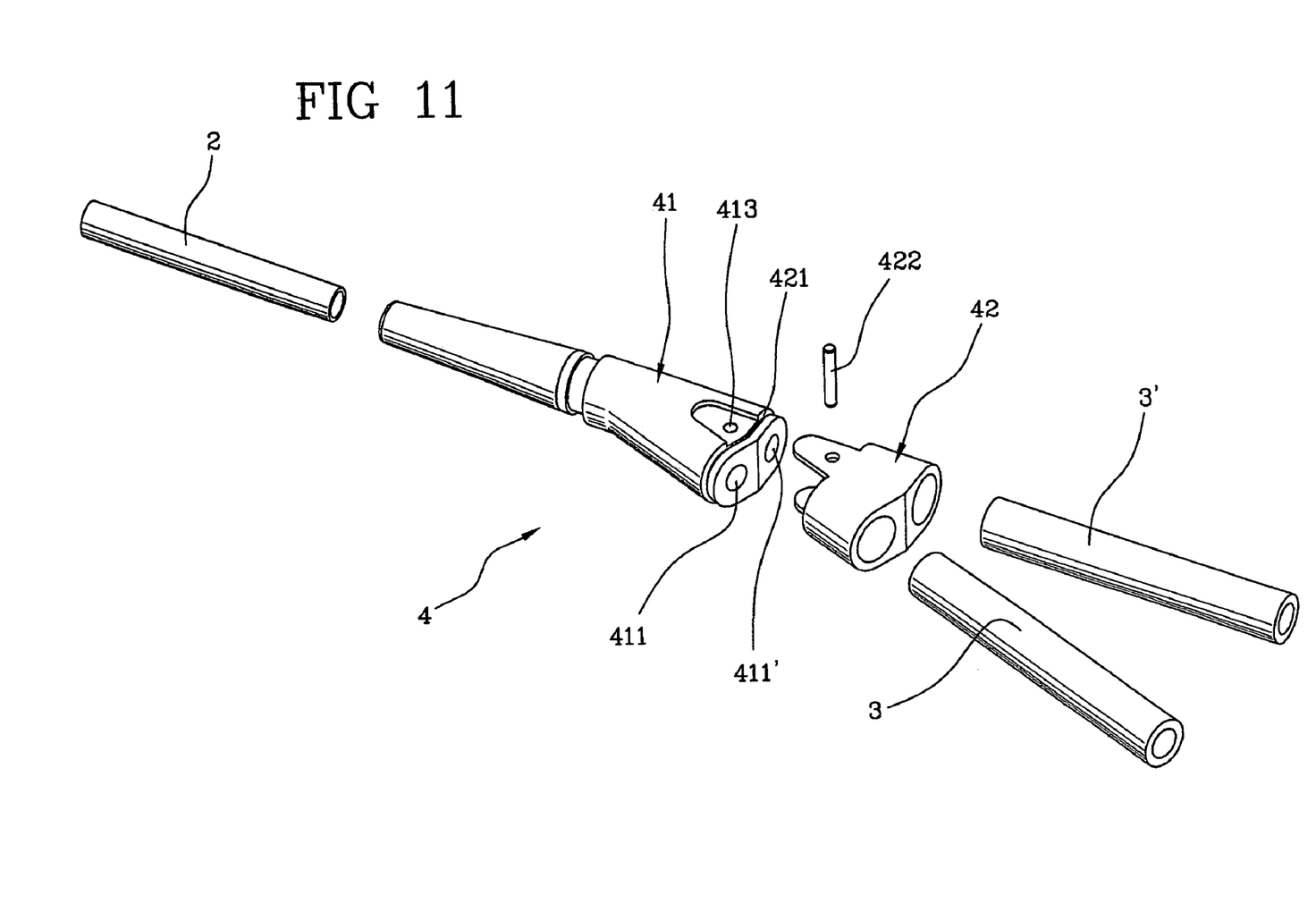

Furthermore, an alternative mechanical connection means between the two connection portions can be envisaged, just as for the single-lumen catheter: the cavity 413 can define a hole traversing at least partially the first connection portion 41 between its first passage 411 and its second passage 411' according to an axis transverse to the longitudinal axis of the first lumen 22. An embodiment of this type of mechanical connection is shown in FIG. 9.

The mechanical connection means above described can be combined: the cavity 413 defines a hole traversing at least partially the first connection portion or hub 41 in an area between its first passage 411 and its second passage 411' according to an axis transverse to the longitudinal axis of the first lumen 22; the auxiliary cavity 412 extends on the hub 41 around the first and second passage 411, 411'; the auxiliary protuberance 421 overmolded on hub 41 just fits into cavity 412.

Notice that connection tubes are not parallel. In the disclosed embodiment, the first connection tube 3 is substantially coaxial to the cannula, while the second connection tube 3' is at an angle alpha to the axis of the cannula alpha between 10 and 30 degrees, for instance equal to 20°. Of course the first tube could be coaxial to cannula axis and the second tube inclined, or according to a further alternative both tubes could be inclined with respect to the canola axis.

Manufacturing Process for Single-Lumen Catheters

The invention also relates to the manufacturing process for manufacturing above described single lumen catheter for vascular access. The method comprises the following stages: taking cannula 2 that has at least one first lumen 21, taking at least one first connection tube 3, positioning in a mould system at least one end of the cannula 2 and at least one end of the first connection tube 3, injecting a molding material to obtain connection means 4 between the end of the first connection tube 3 and the end of the canola, said connection means also placing the first lumen 21 and at least the first tube 3 in fluid communication.

More in detail the method can comprise the following substeps: positioning in a first mould at least the end of the cannula 2, inserting a core into at least the first lumen 21 of the cannula 2 (notice this could be done before or after positioning the canola in the mould), injecting into the first mould a molding material to obtain a first connection portion 41 defining the hub and forming at least one first passage 411 communicating with the first lumen 21 of the cannula; withdrawing the core from the cannula; inserting an auxiliary core in at least the first connection tube 3 and in at least one part of the first outlet port 411 of the first connection portion; placing at least one part of the group constituted by the first connection portion 41 and by at least the first connection tube 3 in a second mould, injecting into the second mould a molding material to obtain a second connection portion 42 molded to connect at least one part of the first connection portion 42 and at least one part of the first connection tube 3. Notice that the second injection forming the portion 42 is done once the first portion has been sufficiently stabilized and solidified to be extracted from first mould and moved to second mould.

During moulding of hub 41 in the first mould, cavity 412 and/or cavity 413, as the case may be, are obtained on the first connection portion 41. Analogously during formation of second portion by injection into the second mould, protuberance 421 and/or protuberance 422 are obtained as per the embodiments above disclosed in detail.

The Manufacturing Process for Dual-Lumen Catheters:

In the embodiments where the catheter comprises at least one second lumen 22 in the cannula 2 and at least one second connection tube 3', then the manufacturing process steps are substantially the same above described but for the following few aspects. During positioning in the first mould, at least one end of the second connection tube 3' is properly placed into the mould; then injecting into the mould enables the connection means 4 to be obtained in which the second lumen 22 of the cannula is in fluid communication with at least the second connection tube 3' via the respective second passage 411'.

More in detail, when placing the cannula in the first mould it is necessary to position at least the end of the cannula 2 with a respective core inserted into each lumen (21, 22) of the cannula 2. Then it is necessary to close the mould and proceed by injecting into the first mould a molding material to obtain the first connection portion 41; after that, the two cores are withdrawn from the cannula; then it is possible to proceed with the overmolding of second portion 42, of course once the first portion sufficiently stabilizes. The first connection portion 41 and the first and second connection tubes (3, 3') ends, provided with respective cores, are then placed in a second mould. Each core interests the respective tube and goes partially into passage 411, 411'. Then a molding material is injected to obtain the second connection portion 42 connecting at least one part of the first connection portion or hub 41 to the tubes 3, 3'.

As for single lumen catheters, during moulding of hub 41 in the first mould, cavity 412 and/or cavity 413, as the case may be, are obtained on the first connection portion 41. Analogously during formation of second portion by injection into the second mould, protuberance 421 and/or protuberance 422 are obtained as per the embodiments above disclosed in detail.

According to the invention, the device for implementing the process disclosed above comprises a first mould, a second mould and the necessary cores for establishing the cavities and avoiding material entering into the cannula lumen(s) or into the tubes during the molding process as above described.

The entire detailed disclosure relates to a single-lumen cannula and a dual-lumen cannula. In the case of dual lumena, the embodiment shown presents a cannula having a cross section where each lumen has a D shape: in detail the lumena of the represented cannula present mutually facing straight portions of the D lumena.

However, it is to be understood that the shape of the cross section could be different without deparing from the scope of the claims. Moreover the invention naturally also applies to catheters with triple lumena. A third connection tube is thus connected to the hub and may be of a different diameter and material then the others.

Figure 5:
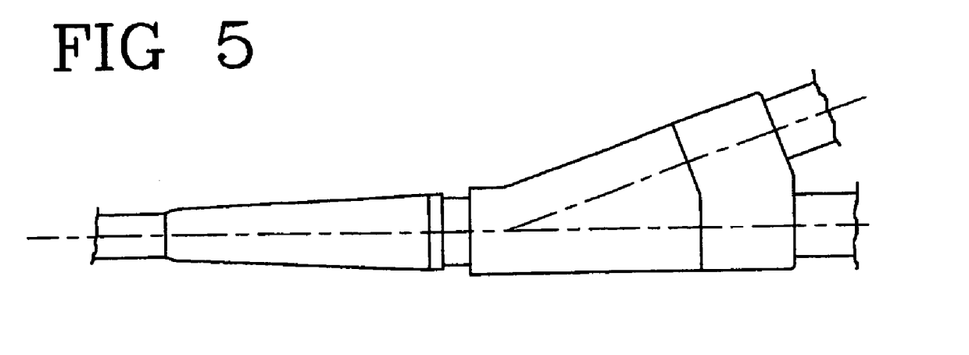
FIGS. 5, 6 and 7 show a partial front view of three embodiments of a catheter according to the invention with a dual-lumen cannula.
Figure 6:
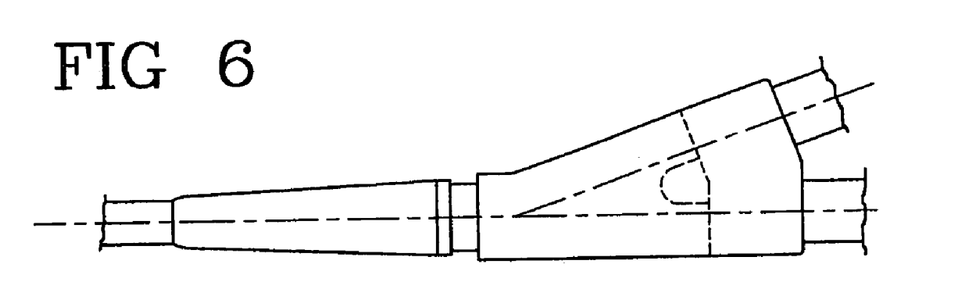
Figure 7:
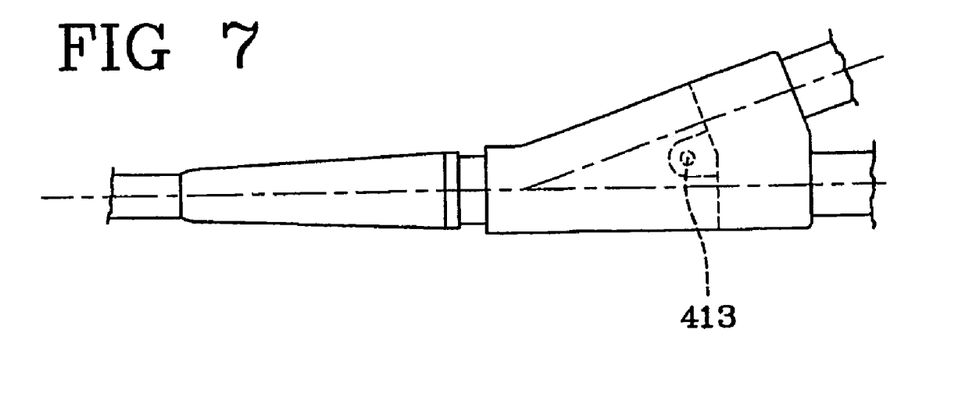
Figure 8:
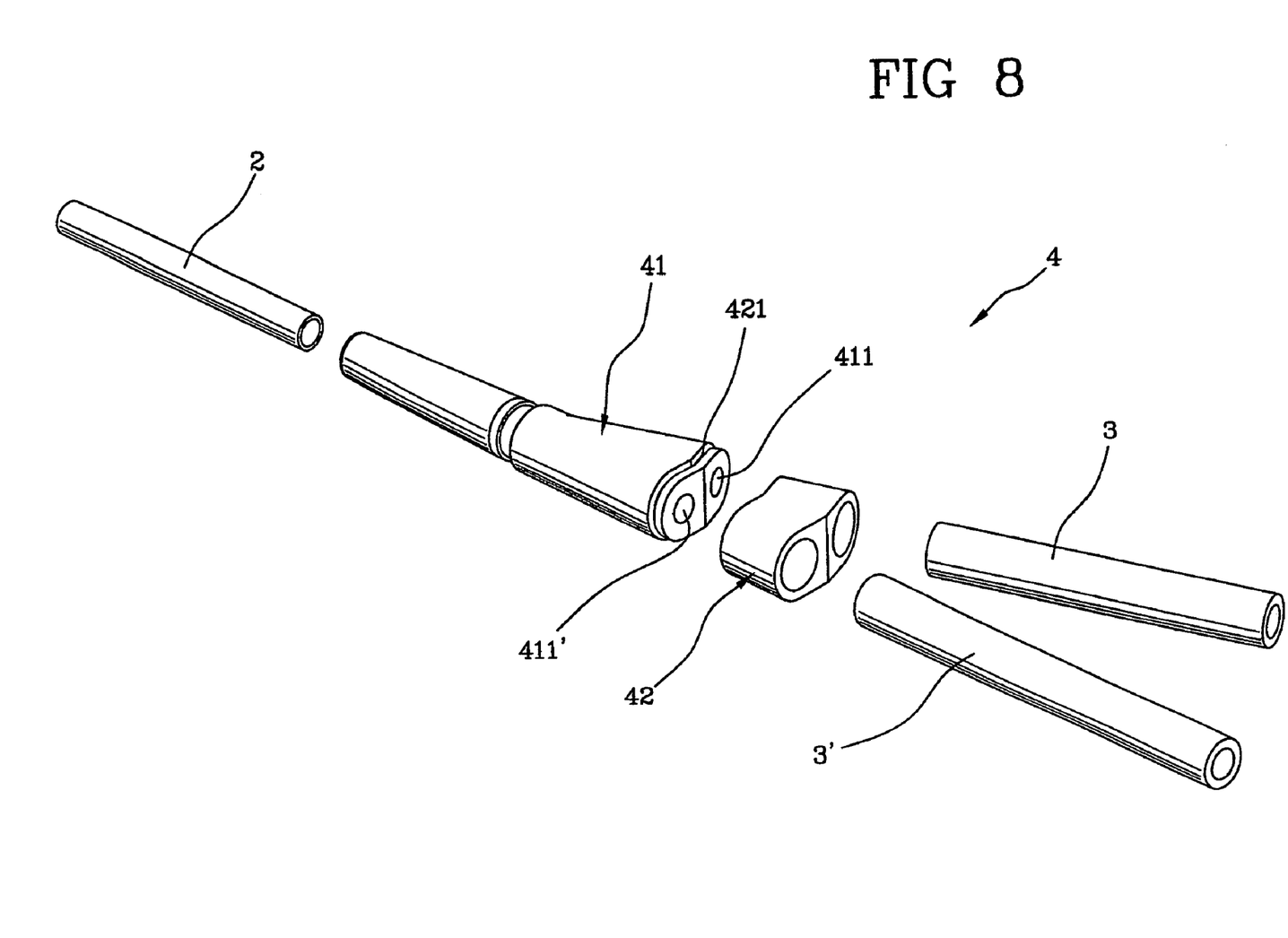
FIGS. 8, 9, 10 and 11 show an exploded view of four embodiments of the catheter according to the invention with a dual-lumen cannula.

FIGS. 5, 6 and 7 show the external appearance of the dual-lumen catheters according to the invention. FIG. 7 illustrates a catheter with only double molding; FIG. 8 illustrates the catheter with double molding and formation of the 'incision-bead' type attachment, and FIG. 7 illustrates the catheter with double molding and formation of at least the 'hole-arm' type attachment.

FIGS. 8 to 11 show exploded views of different embodiments of the invention.

The invention achieves several advantages.

No need of any cyclohexanone or other type chemical bonding, so there is no longer any chemical agent that can release to the patient.

No need of any pre-treatment (cleaning for example) before bonding.

A very strong bonding force is obtained among the three components, namely the cannula, the connection body and the connection tube.

No need of extremely accurate tolerances in order to obtain strong connection between tubes and hub.

The mechanical and thermal connection between the hub and the second connection portion enables a high degree of resistance, even in case of non glue-able materials. In particular the overmolding allows obtaining a connection very resistant to chemical solutions, which may be used in medical applications.

Time is gained during the manufacturing process.

The product can be provided with a pleasant aesthetical appearance due to the possibility to play with the molding materials colors;

The product can generate an ideal connection because while the hub can be made in the most suitable material for connection to the cannula and for definition of the fluid passages, the second connection portion may consist of a second material, which better suits with the connection tubes.

Lastly, via the claimed process a number of different catheters can be made having different sizes of connection tubes but the same cannula: this further enhances flexibility of the manufacturing process.

The invention claimed is:
1. A catheter comprising:
a cannula having at least one first lumen;
at least one first connection tube;
a first connection portion molded on an end of said cannula and defining a hub forming at least one first passage communicating with said at least one first lumen and with a tube end of said at least one first connection tube;
a second connection portion molded on at least one part of said hub and on at least one part of said at least one first connection tube, said second connection portion connecting said tube end and said hub;
a mechanical connection arrangement comprising at least one cavity on said first connection portion and at least one protuberance integral to said second connection portion, a shape of said at least one protuberance complementing a shape of said at least one cavity, said at least one cavity having the shape of an incision on at least one part of said first connection portion, said at least one part surrounding said at least one first passage, wherein said at least one cavity surrounds at least said at least one first passage.

2. The catheter of claim 1, wherein said at least one cavity has the shape of a groove in said first connection portion.

3. The catheter of claim 1, wherein said at least one cavity comprises in longitudinal section a first part with a first depth and a second part with a different second depth.

4. The catheter of claim 1, wherein said first connection portion defines a collar of limited axial length extending around said tube end.

5. The catheter of claim 1, wherein said at least one cavity traverses at least partially said first connection portion according to an axis transverse to a longitudinal axis of said at least one first lumen, said at least one protuberance traversing at least partially said at least one cavity.

6. A catheter comprising:
a cannula having at least one first lumen;
at least one first connection tube;
a first connection portion molded on an end of said cannula and defining a hub forming at least one first passage communicating with said at least one first lumen and with a tube end of said at least one first connection tube;
a second connection portion molded on at least one part of said hub and on at least one part of said at least one first connection tube, said second connection portion connecting said tube end and said hub;
a mechanical connection arrangement comprising:
at least one cavity on said first connection portion, said at least one cavity traversing at least partially said first connection portion according to an axis transverse to a longitudinal axis of said first lumen;
at least one auxiliary cavity on said first connection portion;
at least one protuberance integral to said second connection portion and having a shape complementary to said at least one cavity, said protuberance traversing at least partially said cavity;
at least one auxiliary protuberance integral to said second connection portion and having a shape which corresponds to a shape of said at least one auxiliary cavity;
wherein said auxiliary cavity has a shape of an incision on at least one part of said first connection portion surrounding said at least one first passage, and wherein said auxiliary cavity surrounds at least said at least one first passage.

7. The catheter of claim 6, wherein said auxiliary cavity has a shape of a groove obtained in said first connection portion.

8. The catheter of claim 7, wherein said auxiliary cavity comprises, in longitudinal section, a first part with a first depth and a second part with a second depth different from said first depth.

9. A catheter comprising:
a cannula having at least one first lumen and at least one second lumen;
at least one first connection tube in fluid communication with said at least one first lumen;
at least one second connection tube in fluid communication with said at least one second lumen;
a first connection portion molded on an end of said cannula and defining a hub forming at least one first passage communicating with said first lumen and with a first tube end of said first connection tube;
a second connection portion molded on at least one part of said hub and on at least one part of said at least one first connection tube, said second connection portion connecting said first tube end and said hub, said hub forming at least one second passage communicating with said second lumen and with a second tube end of said second connection tube, said second connection portion being molded on at least a part of said first connection tube and on at least a part of said second connection tube, said second connection portion connecting said first tube end and said at least one first passage, said second connection portion connecting said second tube end and said at least one second passage;
a mechanical connection arrangement comprising:
at least one cavity on said first connection portion;
at least one protuberance integral to said second connection portion, said at least one protuberance having a shape which complements a shape of said at least one cavity;
wherein said at least one cavity surrounds said at least one first passage and said at least one second passage, and
wherein said second connection portion defines a collar extending around said first tube end and said second tube end, said collar comprising a first axial tubular element and a second axial tubular element, said first axial tubular element housing said first tube end, said second axial tubular element housing said second tube end, said collar comprising an intermediate joining portion transversely connecting said first axial tubular element and said second axial tubular element.

10. A catheter comprising:
a cannula having at least one first lumen and at least one second lumen;
at least one first connection tube in fluid communication with said at least one first lumen;
at least one second connection tube in fluid communication with said at least one second lumen;
a first connection portion molded on an end of said cannula and defining a hub forming at least one first passage communicating with said first lumen and with a first tube end of said first connection tube;
a second connection portion molded on at least one part of said hub and on at least one part of said at least one first connection tube, said second connection portion connecting said first tube end and said hub, said hub forming at least one second passage communicating with said second lumen and with a second tube end of said second connection tube, said second connection portion being molded on at least a part of said first connection tube and on at least a part of said second connection tube, said second connection portion connecting said first tube end and said at least one first passage, said second connection portion connecting said second tube end and said at least one second passage;

a mechanical connection arrangement comprising:
  at least one cavity on said first connection portion;
  at least one protuberance integral to said second connection portion, said at least one protuberance having a shape which complements a shape of said at least one cavity;
  wherein said cavity traverses at least partially said first connection portion in an area of said hub placed between said at least one first passage and said at least one second passage, said cavity extending according to an axis transverse to a longitudinal axis of said at least one first lumen, and wherein said first connection portion has an auxiliary cavity surrounding said at least one first passage and said at least one second passage, at least one auxiliary protuberance being integral to said second connection portion, said at least one auxiliary protuberance having a shape which corresponds to a shape of said auxiliary cavity.

11. The catheter of claim 9, wherein said second connection tube is in an axis of said cannula and said first connection tube is at an angle to the axis of the cannula comprised between 10 and 30 degrees.

12. The catheter of claim 10, wherein said second connection tube is in an axis of said cannula and said first connection tube is at an angle to the axis of the cannula comprised between 10 and 30 degrees.

* * * * *

UNITED STATES PATENT AND TRADEMARK OFFICE
CERTIFICATE OF CORRECTION

PATENT NO.         : 8,398,612 B2                                                Page 1 of 1
APPLICATION NO.    : 11/718459
DATED              : March 19, 2013
INVENTOR(S)        : Frey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1061 days.

Signed and Sealed this

First Day of September, 2015

Michelle K. Lee
*Director of the United States Patent and Trademark Office*